United States Patent [19]
Henderson

[11] Patent Number: 5,499,531
[45] Date of Patent: Mar. 19, 1996

[54] SYSTEM AND METHOD FOR DETERMINING VOLATILE CONSTITUENTS, VAPOR PRESSURE AND VAPOR EMISSIONS OF LIQUIDS

[75] Inventor: James K. Henderson, New Orleans, La.

[73] Assignee: The Mitre Corporation, Bedford, Mass.

[21] Appl. No.: 404,482

[22] Filed: Mar. 17, 1995

[51] Int. Cl.$^6$ .................................................... G01N 7/00
[52] U.S. Cl. ........................................ 73/64.45; 73/19.01
[58] Field of Search ........................... 73/64.45, 19.01, 73/19.1, 19.12, 23.41, 61.41, 61.43, 61.59

[56] References Cited

U.S. PATENT DOCUMENTS

| | | | |
|---|---|---|---|
| 2,119,786 | 7/1935 | Kallam | 73/50 |
| 3,041,869 | 7/1962 | Spracklen | 73/23.41 |
| 3,150,516 | 9/1961 | Linnenbom et al. | 73/19.01 |
| 3,236,092 | 2/1966 | Carter | 73/23.41 |
| 3,901,062 | 8/1975 | Lynch et al. | 73/64.2 |
| 5,222,032 | 6/1993 | Fleming | 364/502 |
| 5,235,843 | 8/1993 | Langhorst | 73/19.02 |
| 5,390,551 | 2/1995 | Carvajal et al. | 73/863 |

Primary Examiner—Hezron E. Williams
Assistant Examiner—Jay L. Politzer
Attorney, Agent, or Firm—Morton J. Rosenberg; David I. Klein

[57] ABSTRACT

A system (100) is provided for calculating the vapor pressure for a liquid whose composition is unknown. The liquid to be tested is passed through a gas/liquid separator (120) at a substantially constant flow rate and at a predetermined temperature and pressure. The liquid being passed through separator (120) evolves gas which is passed through a gas meter. The liquid passing from separator (120) passes through a flow meter (134). The evolved gas is also coupled to a gas chromatograph (160) for measurement of the gas composition. The measurement data is input to a processor (180) for converging an initial assumed inlet oil composition, with the measured gas composition, gas flow rate, and liquid flow rate using representative constituent equilibrium data to derive the composition of the inlet liquid stream. The converged liquid composition data is then utilized for calculating the vapor pressure or vapor emissions of the liquid.

30 Claims, 2 Drawing Sheets

SYSTEM AND METHOD FOR DETERMINING VOLATILE CONSTITUENTS, VAPOR PRESSURE AND VAPOR EMISSIONS OF LIQUIDS

BACKGROUND OF THE INVENTION

1. Field of the Invention

This invention directs itself to a system and method for determining the volatile constituents and vapor pressure of a liquid whose composition is unknown. In particular, this invention directs itself to a portable test set-up which can be utilized on-line, or configured to duplicate actual process conditions. Still further, this invention directs itself to a test system wherein the fluid to be tested is passed through a gas/liquid separator at a predetermined temperature and under predetermined pressure conditions. The physical properties of liquid exiting the separator is measured and the liquid passed through a flow meter while the gas evolved therefrom is coupled to a gas meter and a gas chromatograph. More in particular, the liquid flow rate, liquid density and molecular weight, the gas flow rate, the gas composition data obtained from the gas chromatograph, as well as the temperature and pressure data are all input to a processor which performs an iterative calculation to compute the composition of the liquid being tested, and from the derived liquid composition, the vapor pressure is then calculated. From the derived composition, the quantities of vapors and other environmental emissions can also be calculated supposing the fluid were to be heated to a temperature at which its vapor pressure exceeds atmospheric pressure and therefore boiling occurs. Further, this invention directs itself to a method of converging the complex multi-component equilibrium calculation data with the measured physical parameter values to derive the composition of the liquid being tested, such liquid composition being determined to produce a gas composition and flow rates which substantially equal the actual measured values.

2. Prior Art

Test methods for determining vapor pressure and related calculations are known in the art. Vapor pressure is important to understand in view of the potential phase changes that can occur with decreases in fluid pressure or increases in fluid temperature. The text "Chemical Principles", published by W. B. Sanders Company (1969) disclosed on Page 247 that " . . . a liquid boils at a temperature at which its vapor pressure becomes equal to the pressure above its surface . . . ". This vapor pressure definition is the same for both pure components and mixtures of different components such as oil. For example, water boils at 212° F. at atmospheric pressure (14.7 psia); yet if placed in a system at 7.5 psia the water will boil at 180° F. since the vapor pressure of water is 14.7 psia at 212° F. and 7.5 psia at 180° F. Likewise, if the oil has a vapor pressure greater than atmospheric it will boil when fed to an atmospheric tank, with the gases evolved becoming a consideration in terms of safety, environmental emissions, and even operations of tanks, pumps, and metering equipment.

The best prior art known to the Applicants include U.S. Pat. Nos. 4,395,503; 4,459,266; 4,460,544; 4,522,056; 4,667,508; 4,799,166; 4,901,559; 5,020,000; 5,301,125; 5,305,231; 5,327,779; 4,783,989; and, 5,172,586.

In some prior art systems, such as that disclosed by U.S. Pat. No. 4,395,903, vapor pressure is determined by off-line, laboratory methods. In such systems, a sample of the liquid is maintained at a predetermined temperature and pressure, while a sample of the hydrocarbon gas mixture is analyzed utilizing a gas chromatograph. The vapor pressure of the mixture is calculated by summing the partial pressures for each of the components of the gas which were determined by the chromatograph. This method fails to consider, however, the relative volume of gas to the relative volume of liquid, which is an important parameter for determining vapor pressure.

In still other systems, such as that disclosed by U.S. Pat. Nos. 4,783,989 and 5,172,586, the vapor pressure of a liquid composition is measured utilizing a sample which is disposed within a cylinder apparatus having a displaceable piston, permitting the chamber containing the liquid under test to be expanded and the resultant change in pressure therein measured and utilized to plot equilibrium pressures versus chamber size, which are subsequently extrapolated to determine the pressure at a chamber size of minimum expansion which approximates the vapor pressure.

In the standardized petroleum industry test, it is very common to determine vapor pressure utilizing the Reid vapor pressure test (ASTM D-323-90) in combination with a nomograph (American Petroleum Institute 2517) for calculating the "True" vapor pressure at a predetermined temperature. However, that "True" vapor pressure process leads to errors on the order of 50%–300% when compared to the system and method of the present invention. In the standardized Reid test, a liquid sample is collected at atmospheric pressure. This introduces the first source of error since the high vapor pressure components escape. The higher the temperature of the sample being collected, the greater this error becomes. The test then proceeds by chilling the sample in an ice bath to which a volume of air, heated to 100° F., is coupled to the liquid containing chamber, the air containing chamber having four times the volume of the liquid containing chamber. The air and liquid constituents are then shaken and put in a bath at 100° F. The pressure within the container is then measured to establish a vapor pressure value. The nomograph is subsequently utilized for adjusting the Reid to estimate the "True" vapor pressure at other temperatures. Since the sample of liquid is of a predetermined volume those constituents which enter the air chamber's gas phase are also lost from the liquid phase by contact mixing with the air, creating another source of error. In addition, the air chamber acts as an expansion damper which further decreases the measurement value of the liquid's vapor pressure. Thus, both the former and latter sources of error contribute to the Reid test value yielding a lower vapor pressure result which even after adjustment by the API 2517 nomograph is lower than that which will actually exist at a predetermined temperature.

Therefore, it is an object of the present invention to provide a system and method for more accurately predicting the vapor pressure for a liquid, and in particular, it is well suited for determining such for complex multicomponent hydrocarbon compositions such as crude oil.

In addition, the method of the present invention determines the volatile components of the liquid from which the vapor emissions of the liquid can be calculated if the vapor pressure exceeds atmospheric at a given storage tank temperature.

SUMMARY OF THE INVENTION

A system for determining the vapor pressure or vapor emissions for a liquid having an unknown composition is provided. The system includes a subsystem for displacing a liquid to be tested at a predetermined constant flow rate, the liquid displacement subsystem having an outlet port. The system further includes a gas/liquid separator having an inlet coupled in fluid communication with the outlet port of the liquid displacement subsystem. The gas/liquid separator has a gas outlet port and a liquid outlet port. The system also includes an assembly (if necessary) for preconditioning the liquid to be tested to a predetermined temperature. The predetermined temperature is established to ensure that measurable vapors are evolved from the gas/liquid separator for metering purposes. The temperature preconditioning assembly includes a heat exchanger for heating or cooling the liquid and is located between the outlet port of the liquid displacement subassembly and the inlet port of the gas/liquid separator. The system includes an assembly for measuring a liquid flow rate which is coupled to the liquid outlet port of the gas/liquid separator. Also included in the system is an assembly for measuring a gas flow rate which is coupled to the gas outlet port of the gas/liquid separator. The system further includes a gas chromatograph having a gas inlet which is coupled in fluid communication with the gas outlet port of the gas/liquid separator for establishing gas composition data for the gas exiting the gas/liquid separator. Still further, the system includes a processor for (1) establishing a composition of the liquid being tested from at least the gas composition data, the measured liquid molecular flow rate, and the measured gas molecular flow rate, and the individual component thermodynamic equilibrium constants as estimated by conventional equations of state, and (2) calculating the vapor pressure or vapor emissions using the established liquid composition and conventional chemical engineering calculation procedures.

DESCRIPTION OF THE PREFERRED EMBODIMENTS

Figure 1:
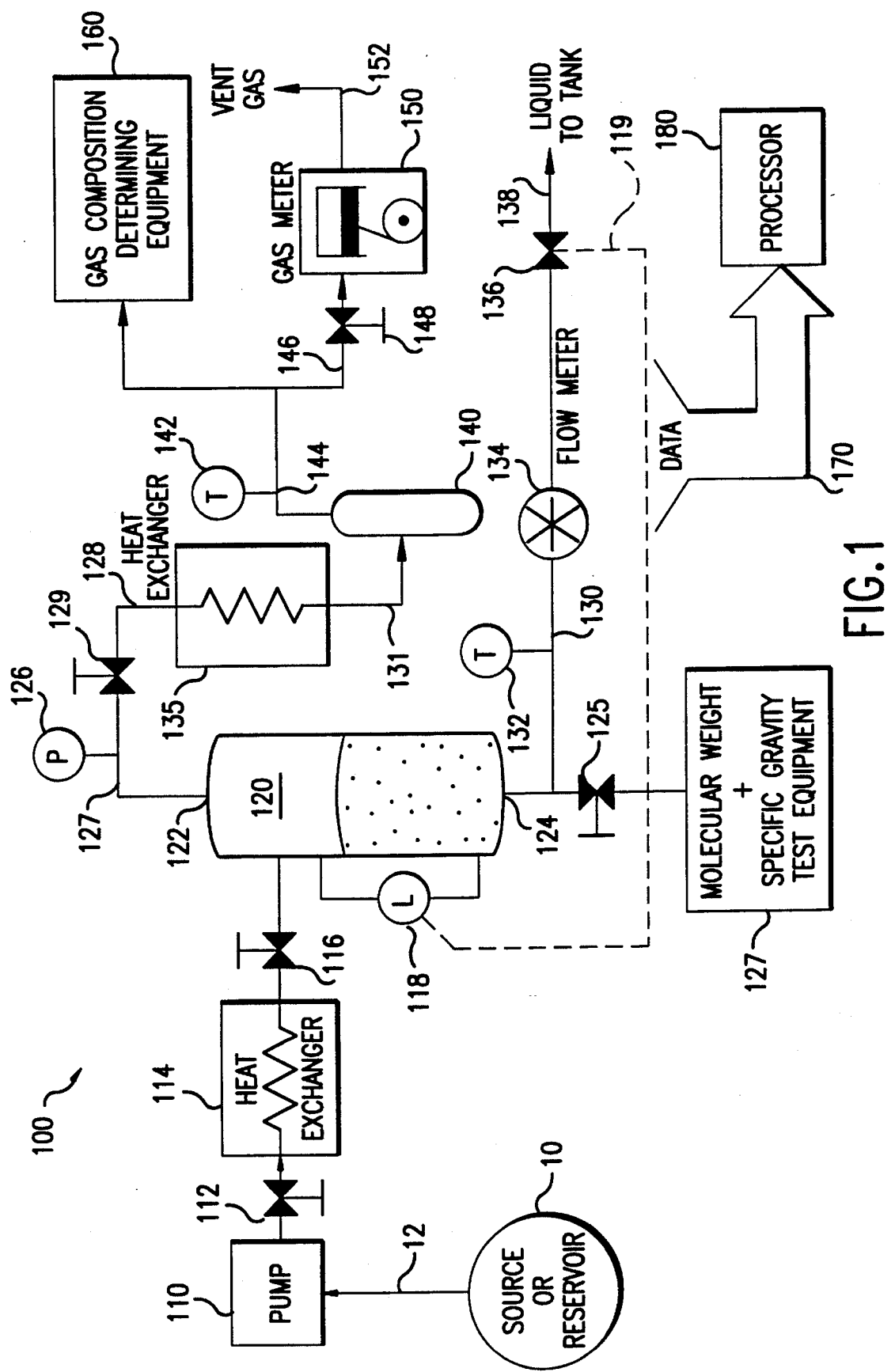
FIG. 1 is a block diagram of the present invention.
Figure 2:
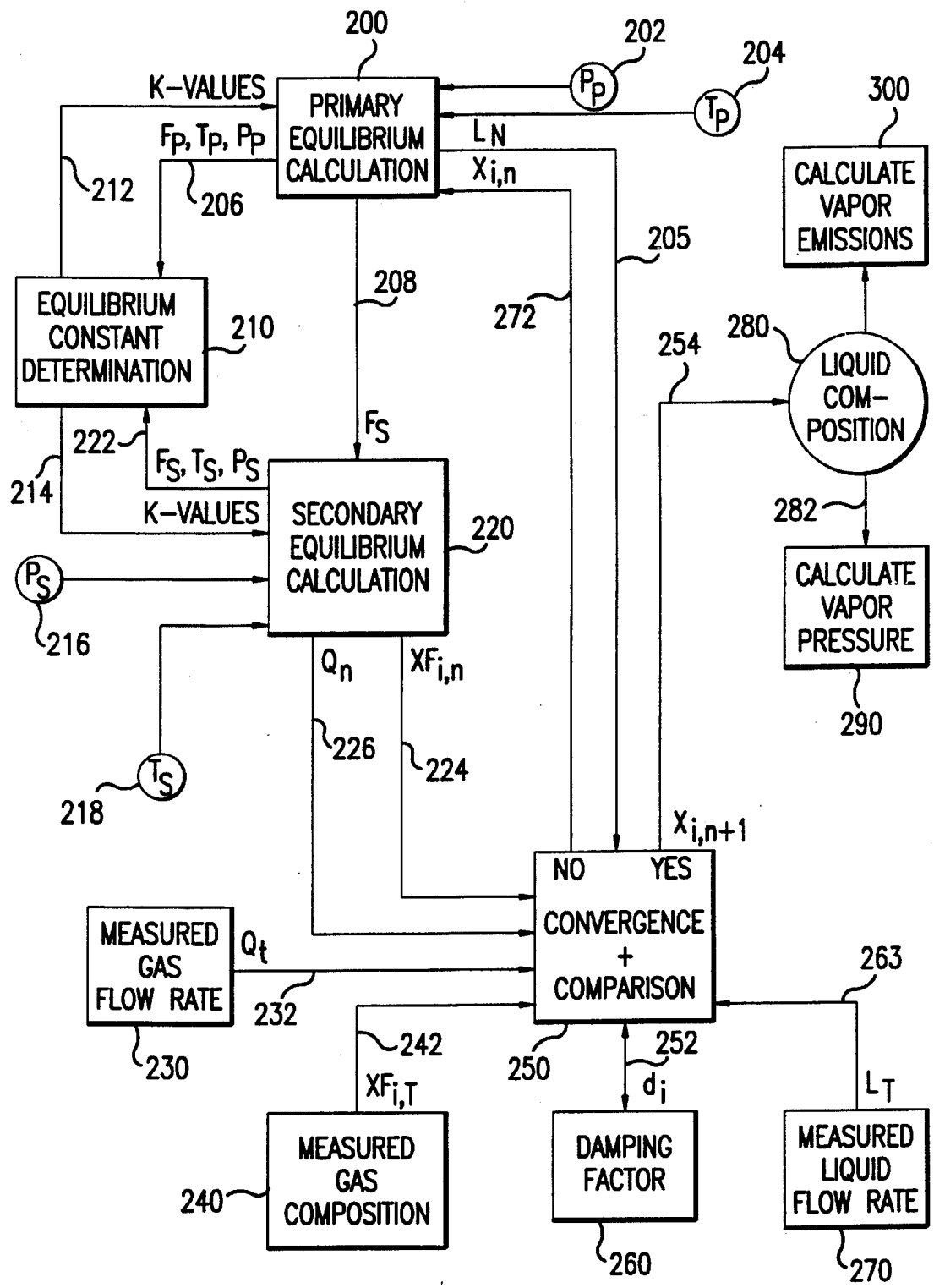
FIG. 2 is a flow diagram of the calculations performed by the processor of the present invention.

Referring now to FIGS. 1 and 2, there is shown system 100 for determining the vapor pressure or vapor emissions for a liquid having an unknown composition. As will be seen in following paragraphs, system 100 is specifically directed to the concept of determining the vapor pressure for hydrocarbon mixtures, such as crude oil, where the precise component fractions are unknown. Although not restricted to use with hydrocarbon liquids, system 10 is particularly adapted for determining the vapor pressure of crude oil where it is particularly important to ensure the safety of personnel and the environment from exposure of the evolved gases from crude oil as the oil experiences both temperature and pressure changes during its transport, storage and processing.

Additionally, system 100 provides for a quick and easy method for determining the vapor pressure or vapor emissions of an unknown liquid composition over a particular temperature range, since once the inlet liquid composition is determined then conventional chemical engineering vapor pressure and vapor emission calculations can be performed at various other temperatures. The method of utilizing system 100 is as an on-line or intermittent test system, wherein the liquid can be tested as it is conveyed between processing points, such as from a reservoir or transport ship to the storage tank facility, or as a simulation thereof. Once the composition of the liquid is determined, the atmospheric vapor emissions to the environment can then be determined. Process simulations of the vapor pressure and emissions can also be performed for any desired temperature range once the inlet composition has been established. Although the specific embodiment disclosed will be discussed in terms of testing crude oil, it should be understood that the system and method for determining the liquid vapor pressure is applicable to any liquid, whether a composition of single or multiple components.

A pump 110 draws crude oil from a source, such as a ship or an underground storage reservoir 10 through a supply line 12. The pump 110 supplies the crude oil to a gas/oil separator 120 at a predetermined substantially constant inlet pressure. The oil, or liquid being tested, may be displaced by means other than pump 110, such as by use of a pressurized fluid, gravity, of the like, to displace the oil. The gas/liquid separator 120 is a conventional separator system, which is sized to provide sufficient flow stream residence time and change in fluid velocities, so as to allow the physical separation of gas and liquid. The oil supplied by pump 110 is conveyed to the separator 120 through a valve 112, heat exchanger 114, and flow control valve 116. The heat exchanger 114, which may be in the form of a heater bath, is adjusted to provide the inlet liquid stream at a predetermined temperature selected from a range of temperatures which is sufficient to vaporize at least some of the inlet liquid components. Control valve 116 is adjusted to provide a substantially constant flow rate through separator 120. A substantially constant liquid level in separator 120 is maintained, which is aided by a liquid level control 118 which is coupled to valve 136 by a signal line 119, the valve 136 being coupled in fluid communication with the liquid outlet conduit 138. Liquid exits the separator 120 through an outlet port 124 for flow through a conduit 130 to a liquid flow meter 134. The temperature of the liquid exiting the separator through the outlet port 124 is monitored by a temperature sensor 132. Valve 125 allows intermittent samples of liquid to be sampled by the equipment for determination of liquid specific gravity and molecular weight 127. The liquid exiting the separator 120 and flowing through the flow meter 134 is carried to a liquid storage tank or other process point by means of a conduit 138 after passage through level control valve 136. Thus, a number of physical parameters of the liquid exiting the gas/liquid separator 120 are measured. Those parameters include the temperature of the liquid, measured by the sensor 132, the flow rate of the liquid, measured by the meter 134 or any other means of measuring liquid flow rate, and the physical properties of the liquid measured by the equipment 127. The specific physical properties which are determined for the liquid exiting the separator are the molecular weight and specific gravity of the liquid.

Gas which separates from the liquid within separator 120 is carried from the gas outlet port 122 to a secondary separator 140 by means of an outlet gas line 127, block valve 129, gas line 128, heat exchanger 135 and gas line 131. The gas pressure is monitored by a pressure sensor 126 coupled to the outlet gas line 127. The pressure of the liquid and gas within system 100 is controlled at a substantially constant level by the operation of pressure control valve 148 which is located on conduit 146. The pressure is typically maintained slightly above atmospheric pressure, to prevent infiltration and contamination by air, however, operation above or below atmospheric pressure is permissible with appropriate leak protection.

The secondary gas/liquid separator functions to provide sufficient gas stream residence time and change in fluid velocities, so as to allow the physical separation of gas and any condensed liquid droplets. Heat exchanger 135, which may be in the form of a cooling water bath, is optionally provided to further regulate temperature of the flow stream to secondary separator 140. The secondary separator gas outlet temperature is monitored by a temperature transducer 142, whose value is subsequently utilized to improve the accuracy of the derived liquid composition and vapor pressure determinations. The gas outlet 144 of secondary separator 140 is coupled to an outlet gas line 146 for coupling to a gas flow meter 150 through the pressure control valve 148. Subsequent to measurement of gas flow rate, the gas is coupled to a gas vent conduit 152, for atmospheric release, combustion, or other processing. Outlet gas line 146 is also coupled to a gas composition sampling system 160, such as a gas chromatograph for analysis of the gas composition components. The types of equipment used to determine the gas composition is not important to the inventive concept and the exemplary use of a gas chromatograph should not be considered a limitation on the invention. Gas chromatograph 160 provides a molecular fraction breakdown of the gas which has evolved from the liquid flowing through separator 120. Thus, a plurality of selected physical parameters of the gas exiting separator 140, which also exited separator 120, are measured. These physical parameters include the pressure of the gas measured by the pressure sensor 126, the temperature of the gas measured by temperature sensor 142, the flow rate of the gas measured by meter 150, and the composition of the gas determined by the gas chromatograph 160. It should be understood that any method of measuring gas flow rate may be used in place of meter 150.

The primary and secondary separator temperatures and pressures, the metered liquid flow rate, the metered gas flow rate, the liquid outlet molecular weight and specific gravity, and the gas composition are all input to a processor 180 for analysis. Such data may be collected automatically utilizing well known data logging systems, or manually entered through a keyboard coupled to processor 180. Although not important to the inventive concept, processor 180 may be a personal-type computer such as those available from such manufacturers as IBM and APPLE Corporations.

The data collection equipment, heater or cooling baths 114 and 135, separators 120 and 140, flow meters 134 and 150, temperature sensors 132 and 142, and pressure sensor 126 may be provided on a test skid to permit easy transport to any of a number of test sites. The test skid is designed to provide a flow stream of crude oil from a selected oil source, such as a cavern reservoir, at a predetermined temperature and pressure into a gas/liquid separator. The test skid is provided with sufficient thermal insulation to minimize ambient heat transfer. This liquid flow test arrangement provides a virtual process duplication of the normal flow of oil into an atmospheric tank, the release of oil vapors from atmospheric tanks being the primary concern requiring a vapor pressure property specification for safety of both the environment and personnel, although other process conditions can be duplicated.

As discussed, the flow rate of the test skid separated gases is measured utilizing a commercially available gas meter. The oil flow rate flowing from the liquid outlet port 124 is measured utilizing a commercially available flow meter. The flow of crude oil into the separator is held at a predetermined rate to maintain a constant flow rate through the separator and provide sufficient residence time, on the order of 3–5 minutes, to allow both liquid and gaseous phases to establish equilibrium conditions and physically separate. System 100's control variables include the gas/oil separator temperature, the separator operating pressure, and the crude oil flow rate. The gas/oil separator temperature is controlled by means of the hot water bath preheater 114 which automatically provides control of the oil separator temperature. The operating pressure of the separator is controlled by controlling the flow of gas exiting the separator, such as by means of the control valve 148. The (optional) heat exchanger, or cooling bath, 135 may be used to control the temperature of secondary separator 140 as measured by temperature transducer 142. The crude oil flow rate is controlled by the inlet control valve 116. The liquid level control 118 and its associated control valve 136 control the liquid level in the separator 120, which is maintained constant.

Having measured particular physical parameters of both the liquid and gas passing through the separators 120 and 140, such may be processed to converge that data on a specific inlet liquid composition where the gas and liquid meter rates, the gas composition, and the associated individual component equilibrium data for that liquid matches the measured data. Once the inlet composition is determined, then it is a simple matter of calculating the vapor pressure of the liquid and the atmospheric vapor emissions for any particular temperature.

Referring now to FIG. 2, there is shown, a flow diagram which schematically represents the data manipulations carried out by the processor 180. The first step in the process begins with the primary gas/liquid equilibrium calculation 200. Multi-component mixtures, such as found in crude oil, partition themselves (to a first approximation) into the gas and liquid phases to the concentration fraction that will satisfy both Raoult's and Dalton's Laws simultaneously. Using Raoult's Law, the vapor pressure contribution of each particular liquid component can be determined by the equation:

$$P_i = X_i P_{i(pure)} \tag{1}$$

where:

$P_i$=vapor pressure contribution of component i to the total liquid vapor pressure (psia);

$X_i$=molecular fraction of component i in the liquid; and, $P_{i(pure)}$=vapor pressure of pure component i at the given liquid temperature (psia).

Further, from Dalton's Law of Partial Pressures, it is known that the vapor pressure contribution of a component is directly proportional to the molecular fraction of that component in the gas phase, by the equation:

$$P_i = Y_i P_{sys} \tag{2}$$

where $Y_i$=molecular fraction of component i in the gas phase; and, $P_{sys}$=total pressure of oil vapor system (psia).

Since at equilibrium both equations are satisfied simultaneously, and both equal $P_i$, then:

$$Y_i P_{sys} = X_i P_{i(pure)} \tag{3}$$

which equates to the following equation:

$$Y_i/X_i = P_{i(pure)}/P_{sys} \tag{4}$$

where, the term $P_{i(pure)}/P_{sys}$ represents a constant for a particular component at a given pressure, temperature and composition. This term is known as the K-value or equilibrium constant for that particular component at that given system pressure, temperature and composition.

Methods for estimating the K-value equilibrium relationships (including adjustments of non-idealities) for various chemical engineering applications are well known in the art. Such methods as the Soave-Redlich-Kwong equation of state K-values have been widely used for providing equilibrium constants for molecular fractions of oil. Thus, by providing appropriate inputs to a conventional process simulator, such as CHEMCAD by CHEMSTATIONS, INC., which provides the equilibrium K-values, the gas/liquid equilibrium and mass balance equations can be solved.

Thus, in block 200, the primary separator pressure value ($P_p$) 202 and the primary separator temperature value ($T_p$) 204 are input as is an initial liquid molecular flow rate ($F_p$). The initial liquid molecular flow rate ($F_p$) is an array of molecular flow rates which are estimated for the inlet flow stream, since its actual individual molecular rates are unknown. Since the liquid specific gravity and molecular weight are measured, the liquid meter volume flow rate can be converted to a liquid molecular flow rate. As the flow meter temperature is also known, the conversion of volume flow rate to molecular flow rate can be appropriately temperature compensated. Additionally, since the gas meter pressure, temperatures, and gas composition are known, the gas meter volume flow rate can be converted to a gas molecular flow rate. From the molecular flow rates the percentage composition of each component of the gas and liquid can be determined. Although it is not critical, the inlet flow stream molecular flow rate is usually estimated to be similar to the composition of a liquid previously tested. Thus, the composition of oil drawn from a particular reservoir is estimated by utilizing a composition which was determined for some other oil reservoir, then adjusting the relative mix and characteristics of the non-volatile constituents of the oil until the specific gravity and molecular weight approximate the measured specific gravity and molecular weight of the liquid exiting the gas/liquid separator. There need be no relationship between the reservoirs, the estimated values provide only an initial starting point for the calculations to be performed.

The inlet flow stream molecular flow rate, and the separator temperature and pressure are coupled to block 210 by the coupling line 206. Block 210 represents the operations of the equilibrium constant (K-value) determination, as performed by any conventional chemical process simulator. The computed K-values are transmitted back to block 200 by means of the coupling line 212. The equilibrium calculation performed in block 200, sometimes referred to as a "flash" calculation provides feed stream data ($F_s$) which represents the gas molecular flow rates exiting from the gas/liquid separator 120 (shown in FIG. 1). That data is coupled to the secondary equilibrium calculation 220 by means of the coupling line 208.

The use of the secondary separator 140, and the associated equilibrium calculations performed in block 220 are optional, and not required if the test skid is constructed with sufficient insulation to avoid the incidental cooling which otherwise occurs downstream of the primary separator 120. By including the equilibrium calculations associated with the secondary separator to account for the changes in temperature, and small changes in gas composition and flow rate due to incidental liquid droplet condensation, the accuracy of the derived liquid composition, vapor pressure, and vapor emission determinations are improved. Thus, the secondary separator pressure value ($P_s$) 216, which is essentially equal to the primary separator pressure value 202, and the secondary separator temperature value ($T_s$) 218, which may or may not be equal to the primary separator temperature, are input to block 220. The secondary feed stream data $F_s$, and the temperature and pressure measurement data are coupled to the equilibrium constant determination block 210 by coupling line 222. For these new parameters, new and different equilibrium constants are determined and coupled back to the secondary equilibrium calculation block 220 by coupling line 214.

The equilibrium calculation of block 220 provides an estimated gas flow rate ($Q_n$) on coupling line 226 to the convergence calculation and comparison block 250, and estimated exit gas fractions ($XF_{i,n}$) on coupling line 224 to the convergence calculation and comparison block 250. Further, the measured gas flow rate ($Q_T$) 230 is coupled to the convergence calculation and comparison block 250 by coupling line 232. Likewise, the measured exit liquid meter rate ($L_T$) 270 is coupled to block 250 by coupling line 263 and the calculated liquid meter rate ($L_N$) is coupled to block 250 by coupling line 205. The measured gas composition ($XF_{i,T}$) 240 is transmitted to the inlet composition convergence calculation and comparison block 250 by coupling line 242. The convergence algorithm is performed utilizing an exponential damping factor 260, herein after referred to as a damping exponent, coupled to block 250 by the coupling line 252, the damping exponent being based on the estimated relative gas/oil split for each of the various components. The use of damping factors to prevent oscillation of convergence calculations is well known in the art. The damping factor selected does not affect the final convergence result, it only affects the speed, the number of iterations, in reaching the convergence result. In the present invention use of the estimated gas/oil split provides an arbitrary method of selecting a damping factor, which method has been found to permit the convergence calculations to proceed at a satisfactory speed, and avoid oscillation.

The convergence calculation performed in block 250 systematically brings about a complete convergence with all reasonable test data measurements to define an inlet liquid flow stream whose molecular flow rates are calculated to provide gas molecular flow rates and liquid volume flow rates which substantially equal the measured gas molecular flow rates and liquid volume flow rates at the given temperature and pressure values of the primary and secondary separators. The convergence algorithm is defined by the matrix equation:

$$A_{n+1}=A_n(AF_T/AF_n)[((Q_T/L_T)/(Q_n/L_n))^{d_A}] \quad (5)$$

$$B_{n+1}=B_n(BF_T/BF_n)[((Q_T/L_T)/(Q_n/L_n))^{d_B}]$$

$$C_{n+1}=C_n(CF_T/CF_n)[((Q_T/L_T)/(Q_n/L_n))^{d_C}]$$

$$.=\ldots$$

$$.=\ldots$$

$$X_{n+1}=X_n(XF_T/XF_n)[((Q_T/L_T)/(Q_n/L_n))^{d_X}]$$

where,

A, B, C, ... X equals the molecular flow rate of inlet oil components, A, B, C, ... X;

n=prior estimate input/results subscript;

n+1=updated estimate input subscript;

T=test skid measured subscript;

AF, BF, CF, ... XF=the molecular fraction of exit gas components;

Q=exit gas molecular flow rate;

L=exit liquid volume flow rate; and, $d_A, d_B, d_C, \ldots d_X$ = gas rate damping exponent for components A, B, C, ... X.

This matrix equation can be simplified to:

$$X_{i,n+1} = X_{i,n}(XF_{i,T}/XF_{i,n})[((Q_T/L_T)/(Q_n/L_n))^{d_i}] \quad (6)$$

for i=1 to k
where:

$X_i$ is a molecular flow rate for each inlet liquid component, k is the total number of measured gas components, $XF_i$ is a molecular fraction of each exit gas component, and $d_i$ is a gas rate damping exponent for each measured gas component. It should be noted that the non-volatile components (not measured by the gas chromatograph) will remain unchanged from their initial molecular flow rate assumption.

The computations performed in convergence block 250 results in a calculated flow stream, which is the summation of $(X_{i,n+1})$ for i=1 to k being output on coupling line 254. The calculated values $(Q_n, XF_{i,n}, L_n)$ and the measured values $(Q_T, XF_{i,T}, L_T)$ are then tested within block 250 to determine whether the calculated values are within the appropriate tolerance of the measured values. If they are not, then the newly calculated component values $(X_{i,n+1})$ are input to the primary equilibrium calculation routine of block 200 in place of the values previously estimated for line 272, the summation of $X_{i,n+1}$ being set equal to the inlet liquid molecular flow rate $(F_p)$. The process is then repeated, returning to block 200, wherein each iteration provides a closer match between the calculated and measured values. When the calculated values have come within a specified tolerance of the measured values, then the liquid molecular flow rate data from line 254 is transferred to block 280 where the inlet liquid composition may be output and is then coupled to block 290 where vapor pressure is calculated by conventional chemical engineering methods and/or block 300 where vapor emissions are calculated by conventional chemical engineering methods. Such vapor pressure and vapor emission calculations, where the liquid composition is known, are well known in the chemical engineering art.

An additional features of the system 100 is that it provides an alternative method to conveniently measure a liquid vapor pressure. This liquid vapor pressure measurement at a particular temperature can be accomplished without the necessity of determining the gas composition, gas flow rate, or the liquid flow rate. A continuous liquid flow rate is maintained through separator 120, while the valve 129 is closed to prevent escape of any evolved gases from the liquid flowing through separator 120. Then it is known that the pressure in separator 120 will asymptotically rise with time until the pressure which is measured by the pressure sensor 126 is equivalent to the liquid vapor pressure at the predetermined separator temperature, which is temperature controlled by heat exchanger 114. This independently measured vapor pressure result may be used to check the accuracy of the calculated value from processor 180 for a particular temperature value. Therefore, by adjusting the temperature of the heat exchanger 114 to a desired temperature, while continuously flowing liquid through the separator 120, and while maintaining a constant liquid level in separator 120, the vapor pressure for the particular liquid composition, at the set temperature, can be simply measured by the pressure sensor 126 when at steady-state. This method provides a very efficient means of determining vapor pressure for a known temperature. Such is also important for confirming the results of the vapor pressure calculation performed by processor 180. This method may also be used to measure vapor pressure for a particular temperature using the apparatus of system 100.

Referring to Table 1, there is shown the oil analysis data generated for the primary equilibrium calculation block 200 and secondary equilibrium calculation block 220, as well as the measured gas composition, measured gas flow rate, and measured oil flow rate. The component physical properties of molecular weight and specific gravity are directly available through physical property data books for the higher vapor pressure materials such as nitrogen through benzene. The lower vapor pressure crude oil component's molecular weights and specific gravities can be determined by testing of samples thereof. The equilibrium K-values are estimated from chemical engineering process simulators which have built-in capabilities using thermodynamic equation of state methods to easily predict K-values based upon the given gas/liquid separation conditions of pressure, temperature, and composition. It should also be noted that the system 100 data of gas composition, gas meter rate, and oil meter rate were measured by conventional oil and gas meters and gas chromatographs, as has been previously described.

TABLE 1

OIL ANALYSIS DATA

| | PHYSICAL PROPERTIES | | GAS/LIQUID EQUILIBRIUM PROPERTIES | | GAS COMPOSITION |
| --- | --- | --- | --- | --- | --- |
| | | | Primary Gas/Liquid | Secondary Gas/Condensate | |
| Components | Molecular Weight | Liquid Specific Gravity | Sep. K-Value 130.3° F. 15.7# | Sep. K-Value 86.9° F. 15.7# | ANALYSIS Volume Fraction |
| Nitrogen | 28.0 | 0.8081 | 524.635 | 550.411 | 0.0200 |
| Oxygen | 32.0 | 1.1275 | 318.625 | 299.483 | 0.0004 |
| Carbon Dioxide | 44.0 | 0.8270 | 59.223 | 45.984 | 0.0184 |
| Hydrogen Sulfide | 34.1 | 0.7901 | 27.146 | 18.828 | 0.0401 |
| Methane | 16.0 | 0.3000 | 199.339 | 177.816 | 0.0645 |
| Ethane | 30.1 | 0.3564 | 43.697 | 31.508 | 0.1507 |
| Propane | 44.1 | 0.5077 | 14.426 | 8.970 | 0.2787 |
| Iso-butane | 58.1 | 0.5631 | 6.573 | 3.720 | 0.0670 |
| N-butane | 58.1 | 0.5844 | 4.772 | 2.561 | 0.1784 |
| Iso-pentane | 72.1 | 0.6227 | 2.109 | 1.023 | 0.0574 |
| N-pentane | 72.1 | 0.6307 | 1.662 | 0.775 | 0.0686 |
| Hexanes | 86.2 | 0.6633 | 0.599 | 0.245 | 0.0414 |

TABLE 1-continued

OIL ANALYSIS DATA

|  | PHYSICAL PROPERTIES | | GAS/LIQUID EQUILIBRIUM PROPERTIES | | GAS COMPOSITION |
|---|---|---|---|---|---|
|  |  |  | Primary Gas/Liquid | Secondary Gas/Condensate |  |
| Components | Molecular Weight | Liquid Specific Gravity | Sep. K-Value 130.3° F. 15.7# | Sep. K-Value 86.9° F. 15.7# | ANALYSIS Volume Fraction |
| Benzene | 78.1 | 0.8844 | 0.514 | 0.205 | 0.0144* |
| Toluene | 92.1 | 0.8718 | 0.173 | 0.060 | 1.0000 |
| Xylene | 106.2 | 0.8687 | 0.058 | 0.017 |  |
| Ethyl Benzene | 106.2 | 0.8718 | 0.066 | 0.020 |  |
| C175 | 101.3 | 0.7247 | 0.207 | 0.074 |  |
| C250 | 131.3 | 0.7705 | 0.028 | 0.008 |  |
| C375 | 182.7 | 0.8174 | 0.001 | 0.000 |  |
| C530 | 245.6 | 0.8603 | 0.000 | 0.000 |  |
| C650 | 415.9 | 0.9216 | 0.000 | 0.000 |  |
| C1050 | 867.4 | 1.0290 | 0.000 | 0.000 |  | where: gas flow rate per minute = 4.8595 SCF
oil flow rate per minute = 1.000 barrel
*C7+fractions lumped by gas chromatograph analyzer
# = pressure, PSIA The oil analysis data thus measured or derived is applied to the processor 180 to allow the determination of the inlet liquid molecular flow rate. Table 2 shows the intermediate and final convergence result comparisons between the calculated outlet gas volume fractions and rates and the measured outlet gas volume fraction and rates, as outlined in Table 1. It should be noted that gas volume fractions are equivalent to gas molecular fractions.

System 100 has been tested by evaluating oil stored as part of the Strategic Petroleum Reserve, wherein large volumes of crude oil are stored in underground caverns with the crude oil being pumped from this underground storage to atmospheric storage tanks. Table 3 shows oil from several different cavern sources, the vapor pressure for such oil being determined utilizing system 100 and the processor 180 algorithm outlined in FIG. 2, as well as by conventional Reid

TABLE 2

OIL ANALYSIS CONVERGENCE

| Components | Initial Assumption | | First iteration | | Third iteration | | Final iteration | | Difference from |
|---|---|---|---|---|---|---|---|---|---|
|  | Inlet Liquid Volume Fraction | Outlet Gas Volume Fraction | Inlet Liquid Volume Fraction | Outlet Gas Volume Fraction | Inlet Liquid Volume Fraction | Outlet Gas Volume Fraction | Inlet Liquid Volume Fraction | Outlet Gas Volume Fraction | Measured Outlet Gas Volume Fraction |
| Nitrogen | 0.000054 | 0.037590 | 0.000029 | 0.022658 | 0.000030 | 0.020105 | 0.000030 | 0.020000 | 0.0000 |
| Oxygen | 0.000003 | 0.002156 | 0.000001 | 0.000447 | 0.000001 | 0.000403 | 0.000001 | 0.000400 | 0.0000 |
| Carbon Dioxide | 0.000100 | 0.018967 | 0.000097 | 0.018972 | 0.000100 | 0.018379 | 0.000100 | 0.018400 | 0.0000 |
| Hydrogen Sulfide | 0.000140 | 0.018476 | 0.000302 | 0.040393 | 0.000312 | 0.040130 | 0.000312 | 0.040100 | 0.0000 |
| Methane | 0.000320 | 0.112554 | 0.000186 | 0.070464 | 0.000193 | 0.064700 | 0.000193 | 0.064500 | 0.0000 |
| Ethane | 0.001576 | 0.153484 | 0.001545 | 0.153824 | 0.001597 | 0.150657 | 0.001601 | 0.150700 | 0.0000 |
| Propane | 0.007022 | 0.269552 | 0.007224 | 0.277001 | 0.007450 | 0.278990 | 0.007450 | 0.278701 | 0.0000 |
| Iso-butane | 0.004010 | 0.062816 | 0.004233 | 0.065705 | 0.004368 | 8,066909 | 0.004376 | 0.067000 | 0.0000 |
| A-butane | 0.013874 | 0.166131 | 0.014748 | 0.174577 | 0.015216 | 0.178215 | 0.015239 | 0.178400 | 0.0000 |
| Iso-pentane | 0.011725 | 0.054265 | 0.012264 | 0.055893 | 0.012665 | 0.057322 | 0.012686 | 0.057400 | 0.0000 |
| R-pentane | 0.016951 | 0.062725 | 0.018332 | 0.066734 | 0.018940 | 0.068512 | 0.018970 | 0.068600 | 0.0000 |
| Hexanes | 0.025940 | 0.030139 | 0.035230 | 0.040060 | 0.036576 | 0.041341 | 0.036639 | 0.041400 | 0.0000 |
| Benzene | 0.001476 | 0.002154 | 0.001459 | 0.002082 | 0.001455 | 0.002063 | 0.001455 | 0.002062 | 0.0000 |
| Toluene | 0.004595 | 0.001747 | 0.004542 | 0.001663 | 0.004531 | 0.001641 | 0.004530 | 0.001640 |  |
| Xylene | 0.008040 | 0.000697 | 0.007949 | 0.000639 | 0.007928 | 0.000623 | 0.007927 | 0.000623 |  |
| Ethyl Benzene | 0.001995 | 0.000207 | 0.001973 | 0.000191 | 0.001968 | 0.000187 | 0.001967 | 0.000186 |  |
| C175 | 0.007808 | 0.002742 | 0.016880 | 0.005730 | 0.020973 | 0.007053 | 0.021212 | 0.007130 |  |
| C250 | 0.163478 | 0.003594 | 0.150440 | 0.002962 | 0.145004 | 0.002765 | 0.144595 | 0.002754 |  |
| C375 | 0.165450 | 0.000005 | 0.163565 | 0.000004 | 0.163141 | 0.000004 | 0.163124 | 0.000004 |  |
| C530 | 0.133013 | 0.000000 | 0.131497 | 0.000000 | 0.131157 | 0.000000 | 0.131142 | 0.000000 |  |
| C650 | 0.271502 | 0.000000 | 0.268408 | 0.000000 | 0.267713 | 0.000000 | 0.267684 | 0.000000 |  |
| C1050 | 0.160928 | 0.000000 | 0.159095 | 0.000000 | 0.158683 | 0.000000 | 0.158665 | 0.000000 |  |
| Total Volume Fraction | 1.000000 | 1.000000 | 1.000000 | 1.000000 | 1.000000 | 1.000000 | 1.000000 | 1.000000 |  |
| Total Volume Rate | 1 Barrels | 4.518 SCF | 1 Barrels | 3.971 SCF | 1 Barrels | 4.805 SCF | 1 Barrels | 4.843* SCF | −0.0004 SCF |

*Note: The 4.860 gas/"outlet" oil ratio equals 4.843 gas/"inlet" oil ratio.

methods utilizing a standard American Petroleum Institute (API) nomograph.

TABLE 3

SPR CRUDE OIL VAPOR PRESSURE COMPARISONS*

| Cavern I.D. | BM-103 | BH-106 | BM-2 | BH-101 |
|---|---|---|---|---|
| Oil Type | Sour | Sour | Sweet | Sweet |
| Gas Contamination | High | Medium | High | None (Incoming) |
| Vapor Pressure Results | | | | |
| System 100 | 34.6 | 24.9 | 41.9 | 17.9 |
| Reid/API | 9.3–5.3 | 9.1–7.3 | 12.0–9.5 | 13.0–12.0 |
| 2517 Nomograph | | | | |

*All Vapor Pressures on nominal 100° F. temperature comparison basis.

The Reid/API Nomograph 2517 test method was found to be in the range of 50%–300% in error in determining the vapor pressure of oil. For example, the Table 3 Reid/API vapor pressure results would indicate no vapor emissions, since the vapor pressures are less than atmospheric (14.7 psia). Yet, actual independent environmental lab measurements of emissions produced from displacement of 100,000 barrels of such cavern oils moved to atmospheric storage tanks showed substantial emissions, which were within 5% agreement with the system 100 estimates of 17–18 tons of total emissions produced. Thus, the equipment and test method of system 100 provides a superior tool for prevention of crude oil losses, optimization of vapor pressure product blending, and for the quantification/minimization of toxic and volatilized oil component emissions from atmospheric storage tanks.

Although this invention has been described in connection with specific forms and embodiments thereof, it will be appreciated that various modifications other than those discussed above may be resorted to without departing from the spirit or scope of the invention. For example, equivalent elements or method steps may be substituted for those specifically shown and described, certain features may be used independently of other features, and in certain cases, particular locations of elements or order of method steps may be reversed or interposed, all without departing from the spirit or scope of the invention as defined by the appended Claims.

What is claimed is:

1. A system for determining volatile constituents of an unknown liquid from which vapor pressure and vapor emissions can be determined therefrom, comprising:
    a. means for displacing a liquid to be tested at a predetermined flow rate, said liquid displacement means having an outlet ports;
    b. a gas/liquid separator having an inlet coupled in fluid communication with said outlet port of said liquid displacement means, said gas/liquid separator having a gas outlet port and a liquid outlet port, said gas/liquid separator having a liquid exiting from said liquid outlet port and a gas exiting from said gas outlet port;
    c. means for measuring selected physical parameters of the liquid exiting from said gas/liquid separator being coupled in fluid communication to said liquid outlet port of said gas/liquid separator;
    d. means for measuring selected physical parameters of the gas exiting from said gas outlet port of said gas/liquid separator being coupled in fluid communication to said gas outlet port of said gas/liquid separator, said means for measuring selected physical parameters of the gas including gas sampling means having a gas inlet coupled in fluid communication with said gas outlet port of said gas/liquid separator for establishing gas composition data for gas exiting said gas/liquid separator; and,
    e. processing means for establishing a composition of the liquid being tested from at least the measured selected liquid physical parameters and the measured selected gas physical parameters, said processing means including:
        I. means for establishing an estimated initial liquid component molecular flow rate entering said gas/liquid separator;
        II. means for determining equilibrium constants for said estimated initial liquid molecular flow rate components;
        III. means for calculating selected physical parameters of gas exiting said gas/liquid separator and selected physical parameters of liquid exiting said gas/liquid separator using at least said estimated initial liquid component molecular flow rate and said equilibrium constants; and
        IV means for converging data representing said measured selected physical parameters of liquid exiting said gas/liquid separator, said measured selected physical parameters of gas exiting said gas/liquid separator, and said estimated initial liquid molecular flow rate, with said calculated selected physical parameters of gas exiting said gas/liquid separator and said calculated selected physical parameters of liquid exiting said gas/liquid separator to ascertain an inlet liquid molecular flow rate.

2. The system as recited in claim 1 where said processor means includes means for calculating vapor pressure and vapor emissions from at least the established liquid composition and said selected physical parameters.

3. The system as recited in claim 1 where said means for measuring selected physical parameters of a gas includes a pressure sensor coupled in fluid communication with said gas outlet port of said gas/liquid separator for measuring a gas pressure value therein.

4. The system as recited in claim 3 where said means for measuring selected physical parameters of a gas further includes means for measuring a gas flow rate coupled to said gas outlet port of said gas/liquid separator.

5. The system as recited in claim 4 where said means for measuring selected physical parameters of a liquid includes means for measuring physical properties of the liquid exiting said gas/liquid separator coupled to said liquid outlet port of said gas/liquid separator.

6. The system as recited in claim 5 where said means for measuring physical properties of the liquid exiting said gas/liquid separator includes means for measuring specific gravity and molecular weight of the liquid exiting said gas/liquid separator coupled to said liquid outlet port of said gas/liquid separator.

7. The system as recited in claim 6 where said means for measuring physical properties of the liquid exiting said gas/liquid separator further includes means for measuring a liquid flow rate coupled to said liquid outlet port of said gas/liquid separator.

8. The system as recited in claim 7 where said means for measuring physical properties of the liquid exiting said gas/liquid separator includes a temperature sensor coupled to said liquid outlet port of said gas/liquid separator.

9. The system as recited in claim 8 where said processing means includes means for providing first estimated equilibrium constants and an estimated inlet liquid molecular flow rate for use in providing a calculated liquid composition exiting said gas/liquid separator, a calculated liquid flow rate, a calculated first gas composition exiting said gas/liquid separator, and a calculated first gas flow rate.

10. The system as recited in claim 9 where said processing means includes means for calculating an inlet liquid molecular flow rate entering said gas/liquid separator, said inlet molecular flow rate calculation means performing an iterative calculation to converge at least said calculated liquid flow rate, said calculated first gas composition exiting said gas/liquid separator, and said calculated first gas flow rate with said measured liquid flow rate, said measured gas flow rate, said estimated inlet liquid molecular flow rate and said established gas composition data.

11. The system as recited in claim 10 where said processing means includes means for calculating vapor pressure for said inlet liquid molecular flow rate.

12. The system as recited in claim 10 where said means for converging uses an equation:

$$X_{i,n+1} = X_{i,n}(XF_{i,T}/XF_{i,n})[((Q_T/L_T)/(Q_n/L_n))^{d_i}]$$

for i=1 to k
where:

$X_i$ is a molecular flow rate for each inlet liquid component, k is a total number of inlet liquid components, n is subscript indicating a prior estimate or result, n+1 is a subscript indicating an updated estimate, Q is an exit gas molecular flow rate, L is an exit liquid volume flow rate, $XF_i$ is a molecular fraction of exit gas components, T is a subscript representing measured data, and $d_i$ is a gas rate damping exponent for each $X_i$ component.

13. The system as recited in claim 9 further comprising a gas/condensate separator having an input port coupled in fluid communication with said gas outlet port of said gas/liquid separator and an outlet port coupled in fluid communication with both said gas flow rate measurement means and said gas sampling means.

14. The system as recited in claim 13 where said processing means includes means for providing second estimated equilibrium constants for use in providing said calculated liquid molecular flow rate entering said gas/liquid separator, said calculated liquid flow rate, a second calculated gas composition exiting said gas/condensate separator, and a second calculated gas flow rate.

15. The system as recited in claim 14 where said processing means includes means for calculating an inlet liquid molecular flow rate entering said gas/liquid separator, said inlet molecular flow rate calculation means performing an iterative calculation to converge at least said calculated liquid flow rate, said calculated second gas composition exiting said gas/condensate separator, and said calculated second gas flow rate with said measured liquid flow rate, said measured gas flow rate, said estimated inlet liquid molecular flow rate and said established gas composition data.

16. The system as recited in claim 15 where said processing means includes means for calculating vapor pressure and means for calculating vapor emissions for said inlet liquid molecular flow rate.

17. The system as recited in claim 16 where said means for converging uses an equation:

$$X_{i,n+1} = X_{i,n}(XF_{i,T}/XF_{i,n})[((Q_T/L_T)/(Q_n/L_n))^{d_i}]$$

for i=1 to k where:

$X_i$ is a molecular flow rate for each inlet liquid component, k is a total number of inlet liquid components, n is subscript indicating a prior estimate or result, n+1 is a subscript indicating an updated estimate, Q is an exit gas molecular flow rate, L is an exit liquid volume flow rate, $XF_i$ is a molecular fraction of exit gas components, T is a subscript representing measured data, and $d_i$ is a gas rate damping exponent for each $X_i$ component.

18. The system as recited in claim 1 further comprising temperature regulation means disposed intermediate said outlet port of said liquid displacement means and said inlet port of said gas/liquid separator for establishing a predetermined temperature of the liquid to be tested.

19. The system as recited in claim 18 where said temperature regulating means includes a heat exchanger coupled in fluid communication between said outlet port of said liquid displacement means and said inlet port of said gas/liquid separator for establishing a predetermined temperature of the liquid to be tested.

20. A method for determining volatile constituents of an unknown liquid from which vapor pressure and vapor emissions are determined therefrom, comprising the steps of:

a. providing a liquid to be tested within a predetermined temperature range;

b. providing a gas/liquid separator;

c. passing said liquid to be tested through said gas/liquid separator at a predetermined flow rate;

d. measuring selected physical parameters of liquid exiting said gas/liquid separator;

e. measuring selected physical parameters of gas exiting said gas/liquid separator, said step of measuring selected physical parameters of gas exiting said gas/liquid separator including the step sampling said gas for establishing gas composition data of gas exiting said gas/liquid separator;

f. establishing an estimated initial liquid component molecular flow rate entering said gas/liquid separator;

g. determining equilibrium constants for said estimated initial liquid molecular flow rate components;

h. calculating selected physical parameters of gas exiting said gas/liquid separator and selected physical parameters of liquid exiting said gas/liquid separator using at least said estimated initial liquid component molecular flow rate and said equilibrium constants; and, i. converging data representing said measured selected physical parameters of liquid exiting said gas/liquid separator, said measured selected physical parameters of gas exiting said gas/liquid separator, and said estimated initial liquid molecular flow rate, with said calculated selected physical parameters of gas exiting said gas/liquid separator and said calculated selected physical parameters of liquid exiting said gas/liquid separator to ascertain an inlet liquid molecular flow rate.

21. The method of claim 20 wherein the step of converging data is followed by the step of determining vapor pressure for said ascertained inlet liquid molecular flow rate.

22. The method of claim 20 wherein the step of measuring selected physical parameters of liquid exiting said gas/liquid separator includes the steps of:

a. measuring physical properties of at least a portion of liquid exiting said gas/liquid separator;

b. measuring a flow rate of liquid exiting said gas/liquid separator; and, c. measuring a temperature of liquid exiting said gas/liquid separator.

23. The method of claim 22 wherein the step of measuring physical properties includes the steps of measuring specific gravity and molecular weight of liquid exiting said gas/liquid separator.

24. The method of claim 20 wherein the step of measuring selected physical parameters of gas exiting said gas/liquid separator includes the steps of:

a. determining a composition of the gas exiting said gas/liquid separator;
   b. measuring a flow rate of the gas exiting said gas/liquid separator; and,
   c. measuring a pressure of the gas exiting said gas/liquid separator.

25. The method of claim 24 wherein the step of determining a gas composition includes the steps of:

a. providing a gas chromatograph; and
   b. passing at least a portion of a gas exiting said gas/liquid separator through said gas chromatograph.

26. The method of claim 20 wherein the step of determining equilibrium constants includes the step of predicting equilibrium constants using equation of state methods.

27. The method of claim 20 wherein the step of converging data includes the step of iteratively solving for said inlet liquid molecular flow rate, said inlet liquid molecular flow rate being ascertained when a calculated gas composition, a calculated liquid flow rate and a calculated gas flow rate for a predetermined temperature and pressure substantially matches a measured gas composition, a measured gas flow rate and a measured liquid flow rate.

28. The method of claim 27 where the step of iteratively solving includes the step of using an equation:

$$X_{i,n+1} = X_{i,n}(XF_{i,T}/XF_{i,n})[((Q_T/L_T)/(Q_n/L_n))^{d_i}]$$

for i=1 to k
where:

X$_i$ is a molecular flow rate for each inlet liquid component, k is a total number of inlet liquid components, n is subscript indicating a prior estimate or result, n+1 is a subscript indicating an updated estimate, Q is an exit gas molecular flow rate, L is an exit liquid volume flow rate, XF$_i$ is a molecular fraction of exit gas components, T is a subscript representing measured data, and d$_i$ is a gas rate damping exponent for each X$_i$ component.

29. The method of claim 28 wherein the step of using said equation includes the step of calculating a damping exponent for each measured gas component based on a relative gas/liquid ratio for a respective measured gas component.

30. The method of claim 21 wherein the step of determining vapor pressure includes the steps of:

a. closing off a gas outlet of said gas/liquid separator;
   b. maintaining a predetermined liquid level in said gas/liquid separator substantially constant;
   c. measuring a steady-state gas pressure within said gas/liquid separator while a flow rate of liquid passing therethrough is maintained; and,
   d. comparing said measured steady-state gas pressure with said determined vapor pressure for a selected temperature within said predetermined temperature range.

* * * * *